United States Patent [19]

Yamada et al.

[11] Patent Number: 5,437,815
[45] Date of Patent: Aug. 1, 1995

[54] TOLAN DERIVATIVE, LIQUID CRYSTAL COMPOSITION CONTAINING THE DERIVATIVE, AND LIQUID CRYSTAL DISPLAY DEVICE HAVING THE COMPOSITION

[75] Inventors: Shuhei Yamada; Shuji Ikukawa; Jitsuko Nakayama, all of Nagano, Japan

[73] Assignee: Seiko Epson Corporation, Tokyo, Japan

[21] Appl. No.: 952,980

[22] Filed: Sep. 29, 1992

[30] Foreign Application Priority Data

| | | |
|---|---|---|
| Oct. 2, 1991 [JP] | Japan | 3-255455 |
| Dec. 2, 1991 [JP] | Japan | 3-318063 |
| May 13, 1992 [JP] | Japan | 4-120735 |
| May 25, 1992 [JP] | Japan | 4-131246 |
| Jun. 29, 1992 [JP] | Japan | 4-170328 |

[51] Int. Cl.$^6$ ............ C09K 19/12; C09K 19/52; C07C 25/13; G02F 1/13
[52] U.S. Cl. ............ 252/299.66; 252/299.01; 252/299.61; 252/299.62; 252/299.67; 570/127; 359/103
[58] Field of Search ............ 252/299.01, 299.64, 252/299.65, 299.66, 299.67, 299.61, 299.63; 570/127; 359/103

[56] References Cited

U.S. PATENT DOCUMENTS 5,084,204  1/1992  Reiffenrath et al. ............ 252/299.62
5,198,149  3/1993  Reiffenrath et al. ............ 252/299.61

FOREIGN PATENT DOCUMENTS 0442266   8/1991   European Pat. Off.
1-502908 10/1989   Japan.
8802130   3/1988   WIPO.
8807514  10/1988   WIPO.

*Primary Examiner*—Shean Wu
*Attorney, Agent, or Firm*—Oliff & Berridge

[57] ABSTRACT

A tolan derivative of a formula:

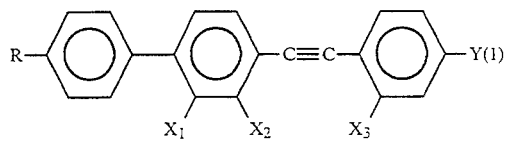

where R represents a linear alkyl group having from 1 to 10 carbon atoms; $X_1$, $X_2$ and $X_3$ independently represent a fluorine atom or a hydrogen atom, provided that one of them is necessarily a fluorine atom and the others are hydrogen atoms; and Y represents a nitrile group or a linear alkyl group having from 1 to 10 carbon atoms; and a liquid crystal composition containing the derivatives; and a liquid crystal display device having the composition are produced. The compound is compatible with other liquid crystal compounds, and by blending the compound with ordinary liquid crystal compounds, a liquid crystal composition having a broadened practical temperature range and an enlarged double refraction anisotropy is obtained.

10 Claims, 1 Drawing Sheet

TOLAN DERIVATIVE, LIQUID CRYSTAL COMPOSITION CONTAINING THE DERIVATIVE, AND LIQUID CRYSTAL DISPLAY DEVICE HAVING THE COMPOSITION

FIELD OF THE INVENTION

The present invention relates to novel tolan derivatives which are used as an electrooptical display material and to liquid crystal compositions containing them and liquid crystal display devices having the compositions.

BACKGROUND

Liquid crystal display devices utilize the electrooptical effect of liquid crystals, and the liquid crystal phases used in them include the nematic phase, the cholesteric phase, and the smectic phase. The display system which is now most widely used is a twisted nematic (hereinafter referred to as TN) type system of utilizing the nematic phase, or a super twisted nematic (hereinafter referred to as STN) type system in which the twisted angle is enlarged.

Because liquid crystal display devices advantageously: i) are small and thin; ii) have a low driving voltage and small power consumption; and iii) do not cause eyestrain even after use for an extended period of time as a result of the image-receiving element, they have heretofore found application in watches, electronic calculators, audio instruments, various metering instruments and car dashboard displays. Recently, in particular, they have been utilized also in displays of personal computers and word processors as well as in color televisions or the like having an extremely large number of pixels, and are therefore especially useful as display devices substitutable for a cathode ray tube. Thus, liquid crystal display devices now find application in various fields, and should find expanded usage in the future.

The following characteristics of liquid crystal materials are considered to be basic and indispensable:

1. Liquid crystal materials are colorless; stable under exposure to heat and light; and stable both electrically and chemically.
2. They have a broad practical temperature range.
3. They have a rapid electrooptical response speed.
4. They require a low driving voltage.
5. The increase of their voltage-light transmittance characteristic is rapid, and the temperature dependence of their threshold voltage ($V_{th}$) is small.
6. They have a broad viewing angle range.

Many conventional liquid crystals are capable of providing characteristic 1, but liquid crystal compounds capable of providing characteristics 2 to 6 in a single component are unknown.

In order to obtain these characteristics, liquid crystal compositions each comprising nematic liquid crystal compounds of plural types or containing both non-liquid crystal compounds and liquid crystal compounds are used. In order to provide characteristic 2, liquid crystal compounds having a low crystal nematic phase transition point (hereinafter referred to as C-N point) and having a high nematic isotropic phase transition point (hereinafter referred to as N-I point) and, as a result, having a broad nematic mesomorphic range, are needed.

With respect to characteristic 3 (response speed, hereinafter referred to as $\tau$), the viscosity coefficient (hereinafter referred to as $\eta$) and the cell gap (hereinafter referred to as d) have the following relative expression:

$$\tau \alpha \eta d$$

Therefore, in order to satisfy characteristic 3, d must be small so as to increase the response speed. In cells for practical use, since the value of $\Delta n \bullet d$ (where $\Delta n$ represents the refractive index anisotropy) is determined to be a constant value in order to prevent generation of interference fringes on the surface of the cell, which would worsen the outward appearance of the cell, the value of d may be reduced when a material having a large $\Delta n$ value is used and, as a result, the response speed may be increased. In order to provide both characteristics 2 and 3, cyclohexyltolan derivatives and phenyltolan derivatives are known as liquid crystal materials having a broad nematic liquid crystal range and a large $\Delta n$ value, as described in JP-A 60-155142 and 60-152427, U.S. Pat. No. 4,713,468 and JP-A 63-152334. (The term "JP-A" as used herein means an "unexamined published Japanese patent application.")

TABLE 1

| | Structural Formula | Transition Point | Reference |
|---|---|---|---|
| a-1 | $C_2H_5$—⟨H⟩—⟨○⟩—C≡C—⟨○⟩—CN | C—N point 135° C.<br>N—I point 250° C. | JP-A 60-155142 |
| a-2 | $C_3H_7$—⟨H⟩—⟨○⟩—C≡C—⟨○⟩—CN | C—N point 153° C.<br>N—I point 265° C. | JP-A 60-155142 |
| b-1 | $C_3H_7$—⟨H⟩—⟨○⟩—C≡C—⟨○⟩—$C_3H_7$ | C—N point 96° C.<br>N—I point 213° C. | JP-A 60-152427 |
| b-2 | $C_3H_7$—⟨H⟩—⟨○⟩—C≡C—⟨○⟩—$C_4H_9$ | C—N point 87° C.<br>N—I point 201° C. | US Pat. No. 4,713,468 |

TABLE 1-continued

| | Structural Formula | Transition Point | Reference |
|---|---|---|---|
| c-1 | C₃H₇–[H]–⟨⟩–C≡C–⟨⟩–C₃H₇ (with F) | C—N point 79° C.<br>N—I point 199° C. | JP-A<br>63-152334 |
| c-2 | C₃H₇–[H]–⟨⟩–C≡C–⟨⟩–C₄H₉ (with F) | C—N point 50° C.<br>N—I point 188° C. | JP-A<br>63-152334 |
| d-1 | C₃H₇–⟨⟩–⟨⟩–C≡C–⟨⟩–C₃H₇ | C—N point 164° C.<br>N—I point 230° C. | JP-A<br>60-152427 |
| d-2 | C₅H₁₁–⟨⟩–⟨⟩–C≡C–⟨⟩–C₃H₇ | C—N point 160° C.<br>N—I point 211° C. | JP-A<br>60-152427 |

Of these compounds, however, cyclohexyltolan derivatives of (a-1) to (c-2) each have a cyclohexane ring in the skeleton, and the ring interferes with the effect of enlarging the value Δn. Compounds (a-1) and (a-2) each have a high C-N point and therefore are considered to have a compatibility problem with other liquid crystal compounds. Compounds (d-1) and (d-2), though having a large Δn value, also have an extremely high C-N point and therefore are also considered to have a compatibility problem.

SUMMARY OF THE INVENTION

An object of the present invention is to provide novel liquid crystal compounds which may be blended with plural kinds of nematic liquid crystals or non-liquid crystals with which they have a high degree of compatibility. The invention provides liquid crystal compositions meeting all practical requirements, including having a broad practical temperature range and a large Δn value.

The compounds of the present invention are compatible with other liquid crystal compounds. By blending them with ordinary known liquid crystal compounds, the resulting mixture may effectively have a broadened practical temperature range and an enlarged Δn value. In these respects, the compounds of the present invention are effective as base components in liquid crystal compositions for an STN display system, which is the primary type of display device employed today.

The present invention provides tolan derivatives of a general formula:

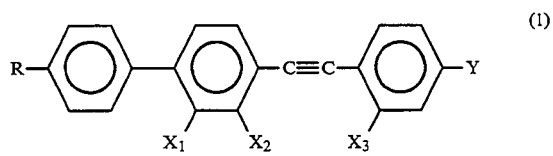

(1)

where R represents a linear alkyl group having from 1 to 10 carbon atoms; $X_1$, $X_2$ and $X_3$ independently represent a fluorine atom or a hydrogen atom, provided that one of them is necessarily a fluorine atom and the others are hydrogen atoms; and Y represents a nitrile group or a linear alkyl group having from 1 to 10 carbon atoms. The invention also provides liquid crystal compositions containing the derivatives and liquid crystal display devices having the composition.

Figure 1:
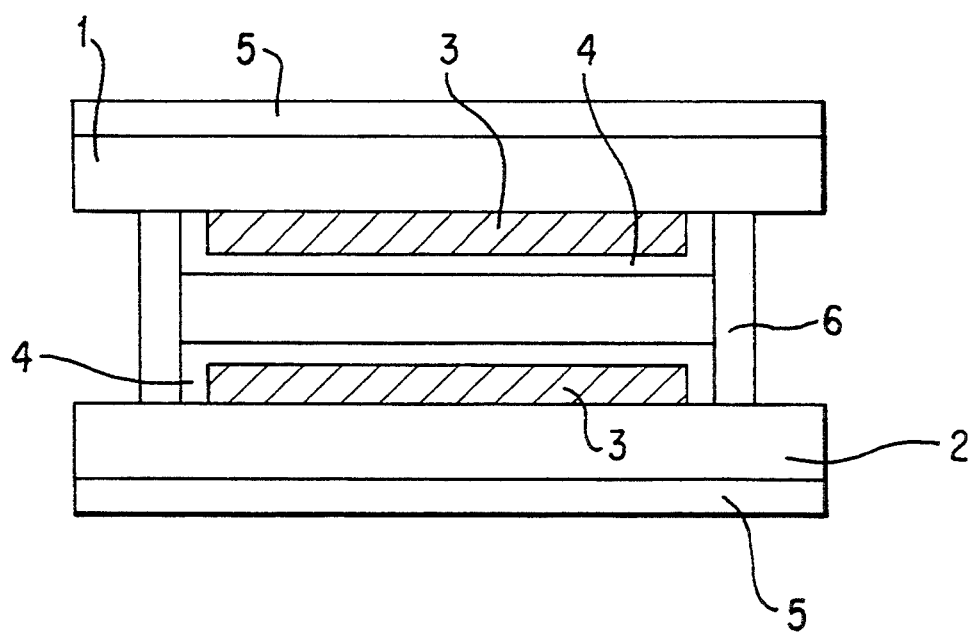
FIG. 1 depicts a liquid crystal display cell as formed in the example of the present invention.

In the drawing, 1 and 2 each are a glass substrate, 3 is a transparent conductive coating, 4 is an aligning coating, 5 is a polarizing plate, and 6 is a sealant.

DESCRIPTION OF PREFERRED EMBODIMENTS

Compounds of the present invention represented by general formula (1) can be obtained by any one of the following processes:

TABLE 2

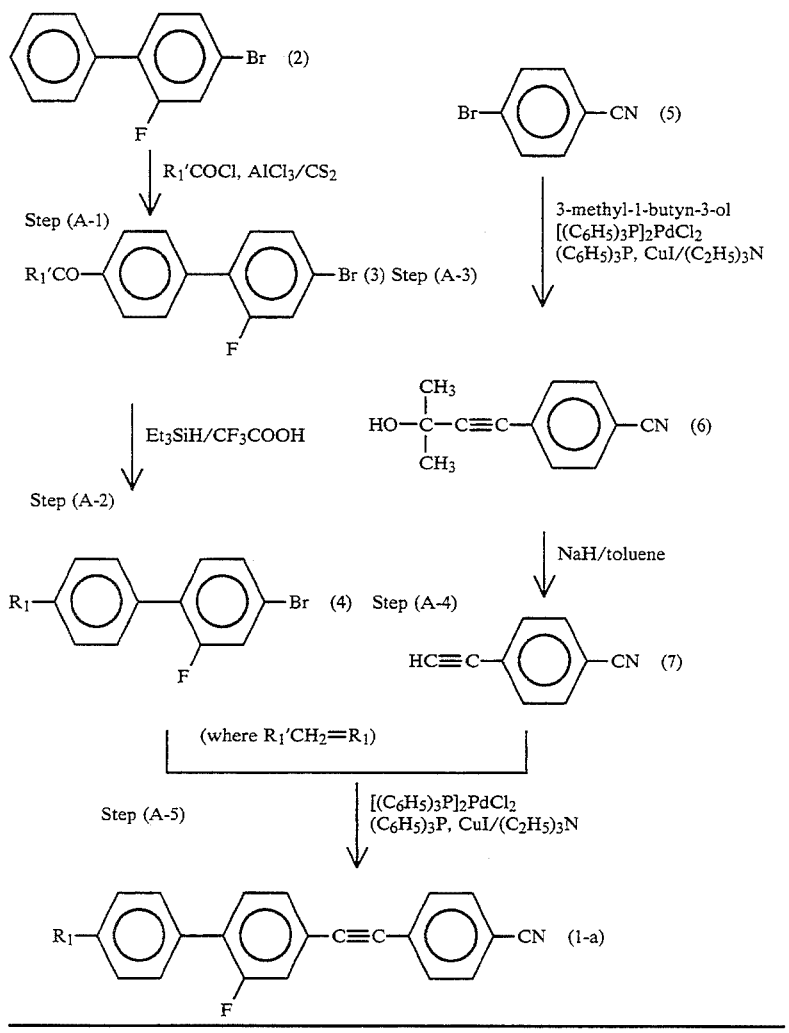

Step (A-1):
Compound (2) is reacted with an alkylcarboxylic acid chloride in carbon disulfide in the presence of aluminium chloride to obtain compound (3).

Step (A-2):
Compound (3) is reacted with triethylsilane in trifluoroacetic acid to obtain compound (4).

Step (A-3):
Compound (5) is reacted with 3-methyl-1-butyn-3-ol in triethylamine in the presence of bis(triphenylphosphine) palladium(II) chloride, triphenylphosphine and copper (I) iodide, to obtain compound (6).

Step (A-4):
Compound (6) is reacted with sodium hydride in toluene to obtain compound (7).

Step (A-5):
Compound (4) is reacted with compound (7) in triethylamine in the presence of bis(triphenylphosphine) palladium(II) chloride, triphenylphosphine and copper(I) iodide, to obtain compound (1-a).

TABLE 3

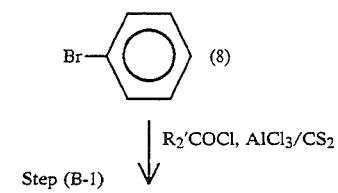

TABLE 3-continued

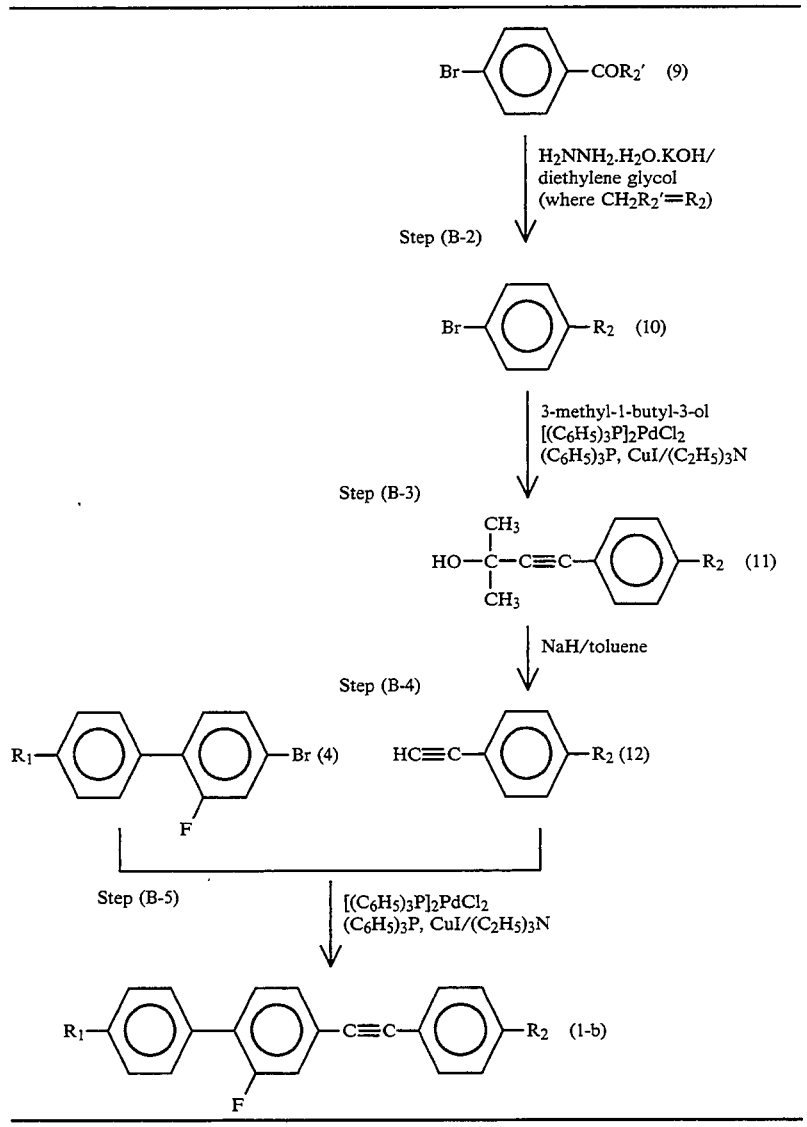

Step (B-1):

Compound (8) is reacted with an alkylcarboxylic acid chloride in carbon disulfide in the presence of aluminium chloride to obtain compound (9).

Step (B-2):

Compound (9) is reacted with hydrazine (monohydrate) in diethylene glycol in the presence of potassium hydroxide to obtain compound (10).

Step (B-3):

Compound (10) is reacted with 3-methyl-1-butyl-3-ol in triethylamine in the presence of bis (triphenylphosphine) palladium(II) chloride, triphenylphosphine and copper(I) iodide to obtain compound (11).

Step (B-4):

Compound (11) is reacted with sodium hydride in toluene to obtain compound (12).

Step (B-5):

Compound (4) is reacted with compound (12) in triethylamine in the presence of bis(triphenylphosphine) palladium(II) chloride, triphenylphosphine and copper (I) iodide to obtain compound (1-b).

TABLE 4

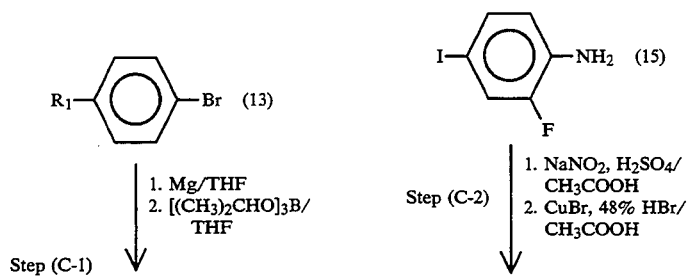

TABLE 4-continued

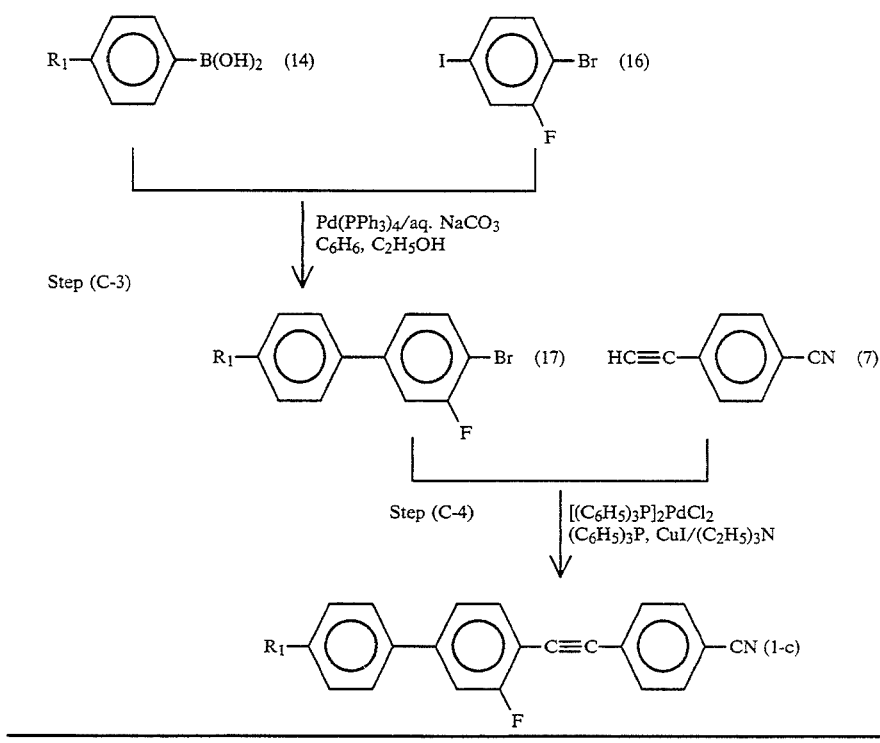

Step (C-1):
Compound (13) is formed into a Grignard reagent in tetrahydrofuran (hereinafter referred to as THF) and then reacted with trimethyl borate to obtain compound (14).

Step (C-2):
Compound (15) is reacted with sodium nitrite and sulfuric acid in acetic acid to give its diazonium salt, which is then reacted with copper (I) bromide and hydrobromic acid to obtain compound (16).

Step (C-3):
Compound (14) and compound (16) are reacted in a mixed solvent of ethanol and benzene in the presence of tetrakistriphenylphosphine palladium(O) to obtain compound (17).

Step (C-4):
Compound (17) is reacted with compound (7) in triethylamine in the presence of bis(triphenylphosphine) palladium(II) chloride, triphenylphosphine and copper(I) iodide to obtain compound (1-c).

TABLE 5

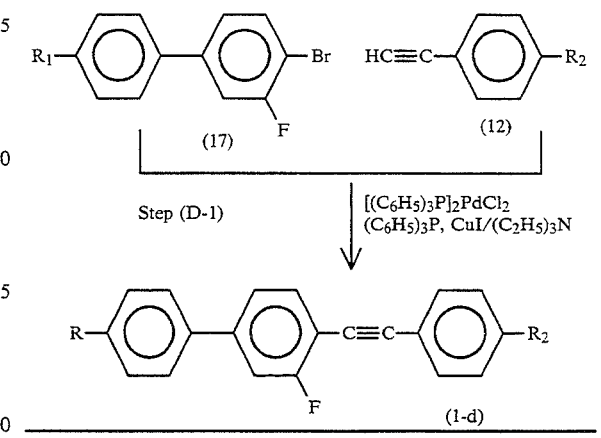

Step (D-1):
Compound (17) is reacted with compound (12) in triethylamine in the presence of bis(triphenylphosphine) palladium(II) chloride, triphenylphosphine and copper(I) iodide to obtain compound (1-d).

TABLE 6

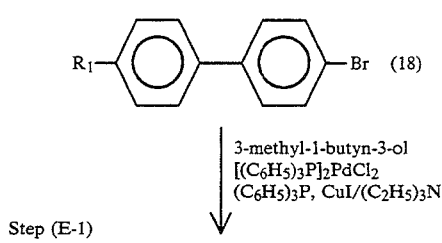

Step (E-1)

TABLE 6-continued

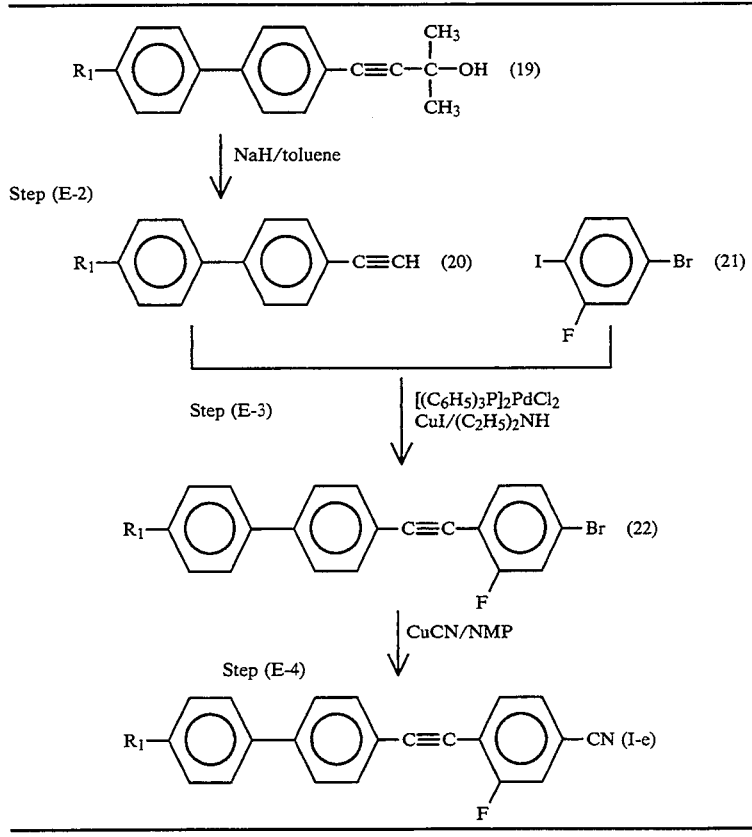

Step (E-1):

Compound (18) is reacted with 3-methyl-1-butyn-3-ol in triethylamine in the presence of bis(triphenylphosphine) palladium(II) chloride, triphenylphosphine and copper(I) iodide to obtain compound (19).

Step (E-2):

Compound (19) is reacted with sodium hydride in toluene to obtain compound (20).

Step (E-3):

Compound (20) is reacted with compound (21) in diethylamine in the presence of bis(triphenylphosphine) palladium(II) chloride and copper(I) iodide to obtain compound (22).

Step (E-4):

Compound (22) is reacted with copper(I) cyanide in N-methylpyrrolidone (hereinafter referred to as NMP) to obtain compound (1-e).

TABLE 7

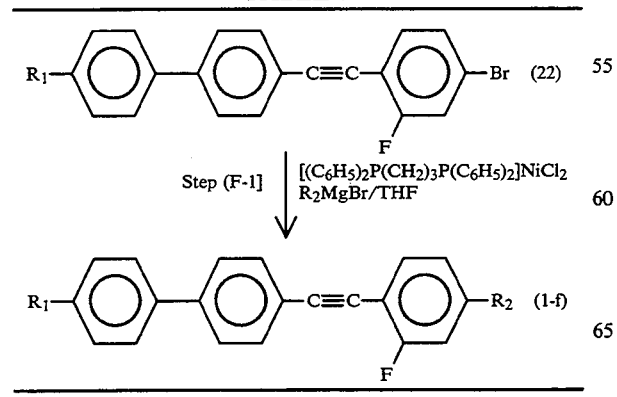

Step (F-1):

Compound (22) is reacted with a Grignard reagent prepared from an alkyl bromide, in THF in the presence of bis(1,3-diphenylphosphinopropane) nickel(II) chloride, to obtain compound (1-f).

Where the tolan derivatives of the present invention are blended to give a liquid crystal composition, the following compounds may be used as a base component of the composition. The illustrated compounds are not intended to be limiting, however, since the tolan derivatives of the present invention are compatible with all conventional liquid crystal compounds and their analogs, and the liquid crystal compositions which are obtained by blending them are characterized as having a broad practical temperature range and a large $\Delta n$ value.

TABLE 8

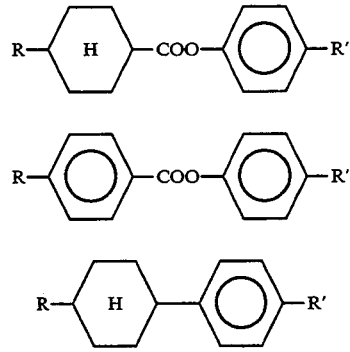

TABLE 8-continued

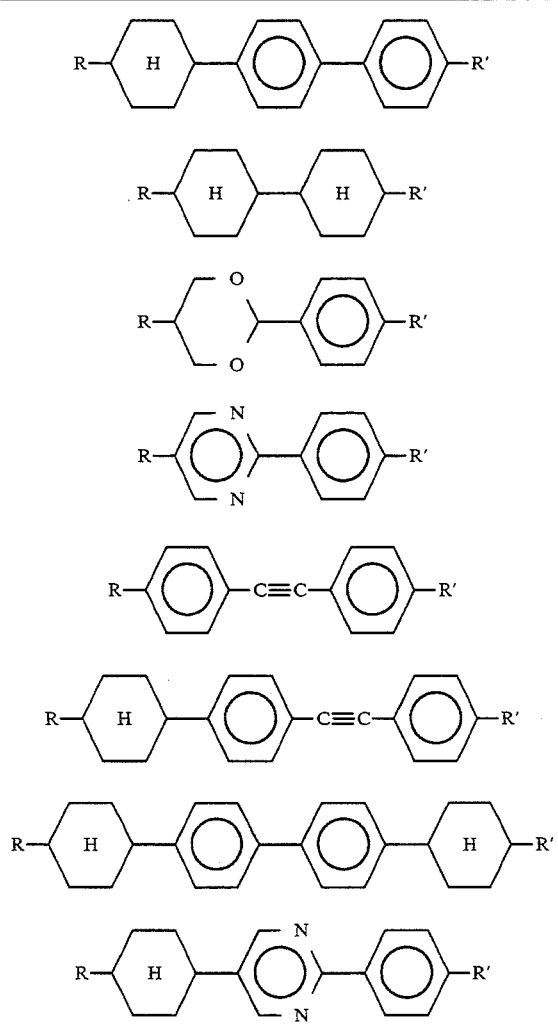

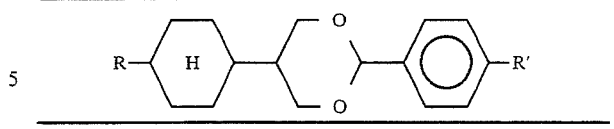

In these formulas, R' represents an alkyl group, an alkoxy group, an alkoxymethylene group, a nitrile group, or a fluoro group, the phenylene group may have a halogen substituent on the 2- or 3-position, and the cyclohexane ring is in the trans-configuration.

The proportion of the compound of the present invention to be in the liquid crystal composition may range from 1 to 50% by weight and is especially preferable in a range of from 1 to 30% by weight in consideration of the precipitation of crystals in a low temperature range.

The most characteristic feature of the compounds of the present invention is introduction of fluorine into the side position of known phenyltolan compounds (e.g., d-1, d-2) to noticeably lower their C-N point and to improve their compatibility with other liquid crystal compounds. Introduction of fluorine into the side position of liquid crystal compounds to lower their C-N point has heretofore been known, but the great depression of the C-N point as exhibited by the compounds of the present invention would not have been expected. For instance, when compound (b-1) is compared with compound (c-1) and compound (b-2) with compound (c-2), the C-N point depression due to fluorine substitution is 17° C. and 37° C., respectively. When compound (e-1) is compared with compound (e-2), compound (f-1) with compound (f-2) and compound (f-3) with compound (f-4), it is only 18° C., 17° C. (28° C. for Sm-N point depression), and 1° C. (48° C. for Sm-N point depression), respectively. In the case of the compounds of the present invention, however, where compound (g-1) is compared with compound (g-2), compound (g-1) with compound (g-3), compound (d-1) with compound (h-1) and compound (d-1) with compound (h-2), great C-N point depression of 49° C., 66° C., 79° C. and 78° C., respectively, is noted. Due to this effect, practical use of phenyltolan derivatives, which have heretofore been difficult to use, has become possible.

TABLE 9

| | Structural Formula | Transition Point | Reference |
|---|---|---|---|
| e-1 | 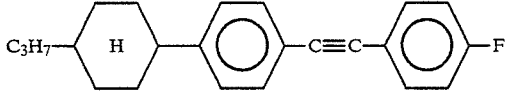 | C—N point 90° C.<br>N—I point 189° C. | JP-A<br>60-155142 |
| e-2 | 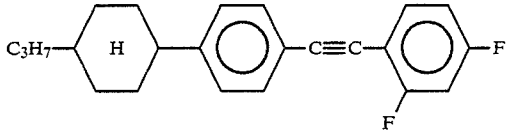 | C—N point 72° C.<br>N—I point 163° C. | JP-A<br>63-287737 |
| f-1 | 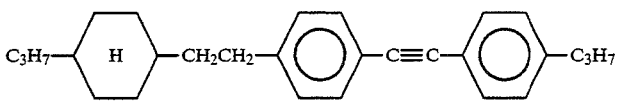 | C—Sm point 67° C.<br>Sm—N point 78° C.<br>N—I point 167° C. | JP-A<br>63-152334 |

TABLE 9-continued

| | Structural Formula | Transition Point | Reference |
|---|---|---|---|
| f-2 | $C_3H_7$—[H]—$CH_2CH_2$—[benzene]—C≡C—[benzene]—$C_3H_7$ (F on first benzene) | C—N point 50° C.<br>N—I point 156° C. | JP-A<br>63-152334 |
| f-3 | $C_3H_7$—[H]—$CH_2CH_2$—[benzene]—C≡C—[benzene]—$C_4H_9$ | C—Sm point 43° C.<br>Sm—N point 90° C.<br>N—I point 159° | JP-A<br>63-152334 |
| f-4 | $C_3H_7$—[H]—$CH_2CH_2$—[benzene]—C≡C—[benzene]—$C_4H_9$ (F on first benzene) | C—N point 42° C.<br>N—I point 149° C. | JP-A<br>63-152334 |

TABLE 10

| | Structural Formula | Transition Point | Remarks |
|---|---|---|---|
| g-1 | $C_3H_7$—[benzene]—[benzene]—C≡C—[benzene]—CN | C—Sm point 174° C.<br>Sm—N point 180° C.<br>N—I point 281° C. | produced by the applicant |
| g-2 | $C_3H_7$—[benzene]—[benzene(F)]—C≡C—[benzene]—CN | C—N point 125° C.<br>N—I point 238° C. | compound (1-a) of the invention |
| g-3 | $C_3H_7$—[benzene]—[benzene]—C≡C—[benzene(F)]—CN | C—N point 108° C.<br>N—I point 256° C. | compound (1-c) of the invention |
| g-4 | $C_3H_7$—[benzene]—[benzene]—C≡C—[benzene(F)]—CN | C—Sm point 151° C.<br>Sm—N point 185° C.<br>N—I point 268° C. | compound (1-e) of the invention |
| d-1 | $C_3H_7$—[benzene]—[benzene]—C≡C—[benzene]—$C_3H_7$ | C—N point 164° C.<br>N—I point 230° C. | JP-A<br>60-152427 |
| h-1 | $C_3H_7$—[benzene]—[benzene(F)]—C≡C—[benzene]—$C_3H_7$ | C—N point 85° C.<br>N—I point 176° C. | compound (1-b) of the invention |
| h-2 | $C_3H_7$—[benzene]—[benzene]—C≡C—[benzene(F)]—$C_3H_7$ | C—N point 86° C.<br>N—I point 197° C. | compound (1-d) of the invention |

TABLE 10-continued

| | Structural Formula | Transition Point | Remarks |
|---|---|---|---|
| h-3 | C₄H₉—⌬—⌬—C≡C—⌬(F)—C₃H₇ | C—Sm point 120° C.<br>Sm—N point 163° C.<br>S—I point 198° C. | compound (1-f) of the invention |

A liquid crystal display device having a liquid crystal composition containing at least one compound of the present invention is suitable as a multiplex driving system device. Through its use, high multiplex driving is possible in TN type and STN type liquid crystal display devices.

The present invention will be explained in more detail by way of the following examples, which are intended to illustrate the invention but are not intended to limit its scope.

Example 1: Production of Compound (1-a)
Production of 3-fluoro-4-(4''-propylphenyl)-4'-cyanotolan:

Step (A-1):

40 g of aluminum chloride and 280 ml of carbon disulfide were taken into a flask, cooled with an ice-salt bath to 0° C. or lower and stirred. A solution of 70 g of 4-bromo-2-fluorobiphenyl as dissolved in 180 ml of carbon disulfide was dropwise added thereto. A solution of 26 g of propionic acid chloride as dissolved in 100 ml of carbon disulfide was dropwise added thereto at 0° C. or lower. After addition, the whole was stirred for 2 hours at 0° C. or lower and then at room temperature overnight. After reaction, the reaction solution was poured into 30 ml of concentrated hydrochloric acid and 300 g of ice and extracted with chloroform. The organic layer was washed three times with water, two times with an aqueous 2% sodium hydroxide solution and then three times with water, and chloroform and carbon disulfide were removed by distillation. The residue was recrystallized from a mixed solvent comprising acetone and methanol to obtain 29 g of 2-fluoro-4-bromo-4'-propionylbiphenyl.

Step (A-2):

29 g of 2-fluoro-4-bromo-4'-propionylbiphenyl was dissolved in 72 ml of trifluoroacetic acid and stirred. 24 g of triethylsilane was dropwise added thereto at room temperature over a period of 30 minutes. After this was stirred for 2 hours, 900 ml of an aqueous saturated sodium hydrogencarbonate solution was dropwise added thereto so that the excess trifluoroacetic acid was decomposed. This was extracted with chloroform and then washed three times with water, and chloroform was removed by distillation. The residue was distilled under reduced pressure (b.p. 140° to 145° C./2 mmHg) to obtain 23.4 g of 2-fluoro-4-bromo-4'-propylbiphenyl.

Step (A-3):

30 g of 4-bromobenzonitrile, 13.4 g of 3-methyl-1-butyn-3-ol, 0.7 g of triphenylphosphine and 0.3 g of bis(triphenylphosphine) palladium(II) chloride were dissolved in 140 ml of triethylamine in nitrogen atmosphere, and 0.1 g of copper(I) iodide was added thereto. This was stirred for one hour at room temperature and then for 5 hours at 90° C. The crystals as precipitated were filtered out and, after triethylamine was removed by distillation, extracted with chloroform. The crystals were washed two times with 10% hydrochloric acid and two times with water, and chloroform was removed by distillation. The residue was distilled under reduced pressure (b.p. 140° to 160° C./5 mmHg) to obtain 23.5 g of 3-methyl-1-(4'-cyanophenyl)-1-butyn-3-ol.

Step (A-4):

23.5 g of 3-methyl-1-(4'-cyanophenyl)-1-butyn-3-ol was dissolved in 250 ml of toluene in nitrogen atmosphere, and 1.6 g of sodium hydride (60% in paraffin liquid) was added thereto. This was stirred for 4 hours at 80° to 90° C. The reaction solution was poured into 300 ml of water, extracted with chloroform, and washed three times with water. Toluene and chloroform were removed by distillation, and the residue was recrystallized from methanol to obtain 9.9 g of 4-cyanophenylacetylene.

Step (A-5):

2.9 g of 2-fluoro-4-bromo-4'-propylbiphenyl, 1.3 g of 4-cyanophenylacetylene, 0.04 g of triphenylphosphine and 0.03 g of bis (triphenylphosphine) palladium(II) chloride were dissolved in 22 ml of triethylamine in nitrogen atmosphere, and 0.01 g of copper(I) iodide was added thereto. This was then refluxed for 5 hours. The reaction solution was poured into 200 ml of water, extracted with chloroform and washed two times with water, and chloroform was removed by distillation. The residue was recrystallized from a mixed solvent comprising acetone and methanol, then purified by silica gel-chloroform column chromatography, and again recrystallized from acetone to obtain 1.9 g of 3-fluoro-4-(4''-propylphenyl)-4'-cyanotolan. The compound had a C-N point of 125.1° C. and an N-I point of 237.6° C.

In the same manner, the following compounds were produced.

3-Fluoro-4-(4''-methylphenyl)-4'-cyanotolan
3-Fluoro-4-(4''-ethylphenyl)-4'-cyanotolan C-N point 163.0° C., N-I point 235.9° C.
3-Fluoro-4-(4''-butylphenyl)-4'-cyanotolan C-N point 75.4° C., N-I point 220.7° C.
3-Fluoro-4-(4''-pentylphenyl)-4'-cyanotolan C-N point 85.6° C., N-I point 218.0° C.
3-Fluoro-4-(4''-hexylphenyl)-4'-cyanotolan
3-Fluoro-4-(4''-heptylphenyl)-4'-cyanotolan
3-Fluoro-4-(4''-octylphenyl)-4'-cyanotolan
3-Fluoro-4-(4''-nonylphenyl)-4'-cyanotolan
3-Fluoro-4-(4''-decylphenyl)-4'-cyanotolan Example 2: Production of Compound (1-b):
Production of 3-fluoro-4-(4''-pentylphenyl)-4'-propyltolan:

Step (B-1):

294 g of aluminium chloride was added to 1000 ml of carbon disulfide and stirred. The reaction solution was cooled to 0° C. or lower, and 166 g of propionyl chloride was dropwise added thereto. Next, 283 g of bromobenzene was dropwise added thereto. Then, the whole was stirred for one hour at room temperature. After reaction, the reaction solution was poured into a mixture of 300 ml of concentrated hydrochloric acid and 600 g of ice. This was extracted with chloroform and washed three times with water, and chloroform was removed by distillation. By distillation under reduced pressure (b.p. 100° to 105° C./2 mmHg), 301 g of 1-bromo-4-propionylbenzene was obtained.

Step (B-2):

301 g of 1-bromo-4-propionylbenzene was dissolved in 1100 ml of diethylene glycol, and 145 ml of hydrazine (monohydrate) and 163 g of potassium hydroxide were added thereto and refluxed for one hour at 130° C. To remove water and hydrazine, the solution was heated up to 190° C. After refluxing for 5 hours at 190° C., this was poured into 2000 ml of water. This was extracted with chloroform and washed three times with water, and chloroform was removed by distillation. By distillation under reduced pressure (b.p. 70° to 75° C./3 mmHg), 252 g of 1-bormo-4-propylbenzene was obtained.

Step (B-3):

60 g of 1-bromo-4-propylbenzene, 38 g of 3-methyl-1-butyn-3-ol, 1.3 g of triphenylphosphine and 0.7 g of bis(triphenylphosphine) palladium(II) chloride were dissolved in 260 ml of triethylamine in nitrogen atmosphere, and 0.2 g of copper(I) iodide was added thereto. This was stirred for one hour at room temperature and for 5 hours at 90° C. The crystals as precipitated were filtered out and, after triethylamine was removed by distillation, extracted with chloroform. These were washed two times with 10% hydrochloric acid and two times with water, and chloroform was removed by distillation. The residue was purified by silicagel-chloroform column chromatography to obtain 37 g of 3-methyl-1-(4'-propylphenyl)-1-butyn-3-ol.

33 g of 3-methyl-1-(4'-propylphenyl)-1-butyn-3-ol was dissolved in 320 ml of toluene in nitrogen atmosphere, and 2 g of sodium hydride (60% in paraffin liquid) was added thereto. This was stirred for 6 hours at 60° C. The reaction solution was poured into 300 ml of water, extracted with chloroform and washed three times with water. Toluene and chloroform were removed by distillation, and the residue was distilled under reduced pressure (b.p. 60° to 63° C./4 mmHg) to obtain 16 g of 4-propylphenylacetylene.

Step (B-5):

4 g of 4'-pentyl-2-fluoro-4-bromobiphenyl, 2.2 g of 4-propylphenylacetylene, 1.05 g of triphenylphosphine and 0.03 g of bis (triphenylphosphine) palladium(II) chloride were dissolved in 27 ml of triethylamine in nitrogen atmosphere, and 0.01 g of copper(I) iodide was added thereto. This was stirred for one hour at room temperature and then for 5 hours at 70° C. The reaction solution was poured into 300 ml of water, extracted with chloroform and washed two times each with water, and chloroform was removed by distillation. The residue was purified by silica gel-chloroform column chromatography and recrystallized from a mixed solvent comprising acetone and methanol to obtain 2.7 g of 3-fluoro-4-(4''-pentylphenyl)-4'-propyltolan. The compound had a C-N point of 74.7° C. and an N-I point of 159.2° C.

In the same manner, the following compounds were produced.

3-Fluoro-4-(4''-methylphenyl)-4'-methyltolan
3-Fluoro-4-(4''-ethylphenyl)-4'-methyltolan
3-Fluoro-4-(4''-propylphenyl)-4'-methyltolan
3-Fluoro-4-(4''-butylphenyl)-4'-methyltolan
3-Fluoro-4-(4''-pentylphenyl)-4'-methyltolan
3-Fluoro-4-(4''-hexylphenyl)-4'-methyltolan
3-Fluoro-4-(4''-heptylphenyl)-4'-methyltolan
3-Fluoro-4-(4''-ocytlphenyl)-4'-methyltolan
3-Fluoro-4-(4''-nonylphenyl)-4'-methyltolan
3-Fluoro-4-(4''-decylphenyl)-4'-methyltolan
3-Fluoro-4-(4''-methylphenyl)-4'-ethyltolan
3-Fluoro-4-(4''-ethylphenyl)-4'-ethyltolan C-N point 121.3° C., N-I point 154.0° C.
3-Fluoro-4-(4''-propylphenyl)-4'-ethyltolan C-N point 105.9° C., N-I point 166.9° C.
3-Fluoro-4-(4''-butylphenyl)-4'-ethyltolan C-N point 76.6° C., N-I point 150.6° C.
3-Fluoro-4-(4''-pentylphenyl)-4'-ethyltolan C-N point 78.9° C., N-I point 154.8° C.
3-Fluoro-4-(4''-hexylphenyl)-4'-ethyltolan
3-Fluoro-4-)4''-heptylphenyl)-4'-ethyltolan
3-Fluoro-4-(4''-octylphenyl)-4'-ethyltolan
3-Fluoro-4-(4''-nonylphenyl)-4'-ethyltolan
3-Fluoro-4-(4''-decylphenyl)-4'-ethyltolan
3-Fluoro-4-(4''-methylphenyl)-4'-propyltolan
3-Fluoro-4-(4''-ethylphenyl)-4'-propyltolan C-N point 92.9° C., N-I point 165.2° C.
3-Fluoro-4-(4''-propylphenyl)-4'-propyltolan C-N point 84.2° C., N-I point 175.5° C.
3-Fluoro-4-(4''-butylphenyl)-4'-propyltolan C-N point 74.3° C., N-I point 160.0° C.
3-Fluoro-4-(4''-hexylphenyl)-4'-propyltolan
3-Fluoro-4-(4''-heptylphenyl)-4'-propyltolan
3-Fluoro-4-(4''-octylphenyl)-4'-propyltolan
3-Fluoro-4-(4''-nonylphenyl)-4'-propyltolan
3-Fluoro-4-(4''-decylphenyl)-4'-propyltolan
3-Fluoro-4-(4''-methylphenyl)-4'-butyltolan
3-Fluoro-4-(4''-ethylphenyl)-4'-butyltolan C-N point 61.2° C., N-I point 149.7° C.
3-Fluoro-4-(4''-propylphenyl)-4'-butyltolan C-N point 60.2° C., N-I point 160.1° C.
3-Fluoro-4-(4''-butylphenyl)-4'-butyltolan C-N point 68.1° C., N-I point 145.9° C.
3-Fluoro-4-(4''-pentylphenyl)-4'-butyltolan C-N point 56.6° C., N-I point 149.5° C.
3-Fluoro-4-(4''-hexylphenyl)-4'-butyltolan
3-Fluoro-4-(4''-heptylphenyl)-4'-butyltolan
3-Fluoro-4-(4''-octylphenyl)-4'-butyltolan
3-Fluoro-4-(4''-nonylphenyl)-4'-butyltolan
3-Fluoro-4-(4''-decylphenyl)-4'-butyltolan
3-Fluoro-4-(4''-methylphenyl)-4'-pentyltolan
3-Fluoro-4-(4''-ethylphenyl)-4'-pentyltolan C-N point 61.3° C., N-I point 152.4° C.
3-Fluoro-4-(4''-propylphenyl)-4'-pentyltolan C-N point 65.4° C. N-I point 162.8° C.
3-Fluoro-4-(4''-butylphenyl)-4'-pentyltolan C-N point 44.7° C., N-I point 150.7° C.
3-Fluoro-4-(4''-pentylphenyl)-4'-pentyltolan C-N point 44.4° C. N-I point 152.8° C.
3-Fluoro-4-(4''-hexylphenyl)-4'-pentyltolan
3-Fluoro-4-(4''-heptylphenyl)-4'-pentyltolan
3-Fluoro-4-(4''-octylphenyl)-4'-pentyltolan
3-Fluoro-4-(4''-nonylphenyl)-4'-pentyltolan
3-Fluoro-4-(4''-decylphenyl)-4'-pentyltolan
3-Fluoro-4-(4''-methylphenyl)-4'-hexyltolan
3-Fluoro-4-(4''-ethylphenyl)-4'-hexyltolan
3-Fluoro-4-(4''-propylphenyl)-4'-hexyltolan
3-Fluoro-4-(4''-butylphenyl)-4'-hexyltolan
3-Fluoro-4-(4''-pentylphenyl)-4'-hexyltolan
3-Fluoro-4-(4''-hexylphenyl)-4'-hexyltolan
3-Fluoro-4-(4''-heptylphenyl)-4'-hexyltolan
3-Fluoro-4-(4''-octylphenyl)-4'-hexyltolan
3-Fluoro-4-(4''-nonylphenyl)-4'-hexyltolan
3-Fluoro-4-(4''-decylphenyl)-4'-hexyltolan
3-Fluoro-4-(4''-methylphenyl)-4'-heptyltolan 3-Fluoro-4-(4"-ethylphenyl)-4'-heptyltolan
3-Fluoro-4-(4"-propylphenyl)-4'-heptyltolan
3-Fluoro-4-(4"-butylphenyl)-4'-heptyltolan
3-Fluoro-4-(4"-pentylphenyl)-4'-heptyltolan
3-Fluoro-4-(4"-hexylphenyl)-4'-heptyltolan
3-Fluoro-4-(4"-heptylphenyl)-4'-heptyltolan
3-Fluoro-4-(4"-octylphenyl)-4'-heptyltolan
3-Fluoro-4-(4"-nonylphenyl)-4'-heptyltolan
3-Fluoro-4-(4"-decylphenyl)-4'-heptyltolan
3-Fluoro-4-(4"-methylphenyl)-4'-octyltolan
3-Fluoro-4-(4"-ethylphenyl)-4'-octyltolan
3-Fluoro-4-(4"-propylphenyl)-4'-octyltolan
3-Fluoro-4-(4"-butylphenyl)-4'-octyltolan
3-Fluoro-4-(4"-pentylphenyl)-4'-octyltolan
3-Fluoro-4-(4"-hexylphenyl)-4'-octyltolan
3-Fluoro-4-(4"-heptylphenyl)-4'-octyltolan
3-Fluoro-4-(4"-octylphenyl)-4'-octyltolan
3-Fluoro-4-(4"-nonylphenyl)-4'-octyltolan
3-Fluoro-4-(4"-decylphenyl)-4'-octyltolan
3-Fluoro-4-(4"-methylphenyl)-4'-nonyltolan
3-Fluoro-4-(4"-ethylphenyl)-4'-nonyltolan
3-Fluoro-4-(4"-propylphenyl)-4'-nonyltolan
3-Fluoro-4-(4"-butylphenyl)-4'-nonyltolan
3-Fluoro-4-(4"-pentylphenyl)-4'-nonyltolan
3-Fluoro-4-(4"-hexylphenyl)-4'-nonyltolan
3-Fluoro-4-(4"-heptylphenyl)-4'-nonyltolan
3-Fluoro-4-(4"-octylphenyl)-4'-nonyltolan
3-Fluoro-4-(4"-nonylphenyl)-4'-nonyltolan
3-Fluoro-4-(4"-decylphenyl)-4'-nonyltolan
3-Fluoro-4-(4"-methylphenyl)-4'-decyltolan
3-Fluoro-4-(4"-ethylphenyl)-4'-decyltolan
3-Fluoro-4-(4"-propylphenyl)-4'-decyltolan
3-Fluoro-4-(4"-butylphenyl)-4'-decyltolan
3-Fluoro-4-(4"-pentylphenyl)-4'-decyltolan
3-Fluoro-4-(4"-hexylphenyl)-4'-decyltolan
3-Fluoro-4-(4"-heptylphenyl)-4'-decyltolan
3-Fluoro-4-(4"-octylphenyl)-4'-decyltolan
3-Fluoro-4-(4"-nonylphenyl)-4'-decyltolan
3-Fluoro-4-(4"-decylphenyl)-4'-decyltolan Example 3: Production of Compound (1-c):
Production of 2-fluoro-4-(4"-propylphenyl-4'-cyanotolan:

Step (C-1):
9.3 g of magnesium was put into a flask in nitrogen atmosphere, and a solution of 68 g of 4-propyl-1-bromobenzene as dissolved in 350 ml of THF was dropwise added thereto. After addition, this was stirred at room temperature overnight to form a Grignard reagent. 70 g of trimethyl borate was dissolved in 38 ml of THF, and the Grignard reagent was dropwise added thereto at room temperature. After addition, this was stirred at room temperature overnight. Next, 75 ml of 10% hydrochloric acid was added thereto and stirred for one hour. This was extracted with chloroform and washed three times with water, and chloroform was removed by distillation to obtain 41 g of 4-propylphenylboric acid.

Step (C-2):
51.2 g of sodium nitrite was dissolved in 390 ml of sulfuric acid, and 454 ml of acetic acid was added thereto at 10° C. or lower. The solution was kept at 20° to 25° C., and 124 g of 2-fluoro-4-iodoaniline was added thereto over a period of one hour and stirred for 2 hours. The solution was dropwise added to a solution of 130 g of copper(I) bromide as dissolved in 390 ml of 48% hydrobromic acid and stirred overnight. Next, 1000 ml of water was added to this, which was then extracted with chloroform and washed three times with water. Chloroform was removed by distillation, and the residue was distilled under reduced pressure (b.p. 120° to 125° C./13 mmHg) and recrystallized from methanol to obtain 114 g of 1-bromo-2-fluoro-4-iodobenzene.

Step (C-3):
A solution of 16.5 g of 4-propylphenylboric acid as dissolved in 130 ml of ethanol was dropwise added to a mixture comprising 30 g of 1-bromo-2-fluoro-4-iodobenzene, 1.6 g of tetrakistriphenylphosphine palladium(O), 186 ml of benzene and 140 ml of 2M aqueous sodium carbonate solution, in nitrogen atmosphere at room temperature. The reaction solution was then refluxed for 5 hours, cooled to room temperature, extracted with chloroform and washed three times with water, and chloroform was removed by distillation. The residue formed was distilled under reduced pressure (b.p. 155° to 170° C./3 mmHg) to obtain 11.7 g of 4-bromo-3-fluoro-4'-propylbiphenyl.

Step (C-4):
2.6 g of 4-bromo-3-fluoro-4'-propylbiphenyl, 1.1 g of 4-cyanophenylacetylene, 0.03 g of triphenylphosphine and 0.03 g of bis(triphenylphosphine) palladium(II) chloride were dissolved in 20 ml of triethylamine in nitrogen atmosphere, and 0.01 g of copper(I) iodide was added thereto. This was then refluxed for 5 hours. The reaction solution was poured into 200 ml of water, extracted with chloroform and washed two times each with water, and chloroform was removed by distillation. The residue was recrystallized from a mixed solvent comprising acetone and methanol, purified by silica gel-chloroform column chromatography and again recrystallized from a mixed solvent of acetone and methanol to obtain 0.8 g of 2-fluoro-4-(4"-propylphenyl)-4'-cyanotolan. The compound had a C-N point of 108.0° C. and an N-I point of 256.1° C.

In the same manner, the following compounds were produced.
2-Fluoro-4-(4"-methylphenyl)-4'-cyanotolan
2-Fluoro-4-(4"-ethylphenyl)-4'-cyanotolan
2-Fluoro-4-(4"-butylphenyl)-4'-cyanotolan C-N point 95.0° C. N-I point 240.0° C.
2-Fluoro-4-(4"-pentylphenyl)-4'-cyanotolan C-N point 89.0° C., N-I point 233.5° C.
2-Fluoro-4-(4"-hexylphenyl)-4'-cyanotolan
2-Fluoro-4-(4"-heptylphenyl)-4'-cyanotolan
2-Fluoro-4 -(4"-octylphenyl)-4'-cyanotolan
2-Fluoro-4-(4"-nonylphenyl)-4'-cyanotolan
2-Fluoro-4-(4"-deyclphenyl)-4'-cyanotolan Example 4: Production of Compound (1-d):
Step (D-1):
4.6 g of 4-bromo-3-fluoro-4'-butylbiphenyl, 2.6 g of 4-pentylphenylacetylene, 0.06 g of triphenylphosphine and 0.04 g of bis(triphenylphosphine) palladium(II) chloride were dissolved in 35 ml of triethylamine in nitrogen atmosphere, and 0.01 g of copper(I) iodide was added thereto. This was stirred for one hour at room temperature and then for 5 hours at 70° C. The reaction solution was poured into 300 ml of water, extracted with chloroform and washed two times with water, and chloroform was removed by distillation. The residue was purified by silica gel-chloroform column chromatography and recrystallized from a mixed solvent comprising acetone and methanol to obtain 1.3 g of 2-fluoro-4-(4"-butylphenyl)-4'-pentyltolan. The compound had a C-N point of 50.5° C. and an N-I point of 171.2° C.

In the same manner, the following compounds were produced.
2-Fluoro-4-(4"-methylphenyl)-4'-methyltolan 2-Fluoro-4-(4″-ethylphenyl)-4′-methyltolan
2-Fluoro-4-(4″-propylphenyl)-4′-methyltolan
2-Fluoro-4-(4″-butylphenyl)-4′-methyltolan
2-Fluoro-4-(4″-pentylphenyl)-4′-methyltolan
2-Fluoro-4-(4″-hexylphenyl)-4′-methyltolan
2-Fluoro-4-(4″-heptylphenyl)-4′-methyltolan
2-Fluoro-4-(4″-ocytlphenyl)-4′-methyltolan
2-Fluoro-4-(4″-nonylphenyl)-4′-methyltolan
2-Fluoro-4-(4″-decylphenyl)-4′-methyltolan
2-Fluoro-4-(4″-methylphenyl)-4′-ethyltolan
2-Fluoro-4-(4″-ethylphenyl)-4′-ethyltolan
2-Fluoro-4-(4″-propylphenyl)-4′-ethyltolan
2-Fluoro-4-(4″-butylphenyl)-4′-ethyltolan
2-Fluoro-4-(4″-pentylphenyl)-4′-ethyltolan
2-Fluoro-4-(4″-hexylphenyl)-4′-ethyltolan
2-Fluoro-4-)4″-heptylphenyl)-4′-ethyltolan
2-Fluoro-4-(4″-octylphenyl)-4′-ethyltolan
2-Fluoro-4-(4″-nonylphenyl)-4′-ethyltolan
2-Fluoro-4-(4″-decylphenyl)-4′-ethyltolan
2-Fluoro-4-(4″-methylphenyl)-4′-propyltolan
2-Fluoro-4-(4″-ethylphenyl)-4′-propyltolan
2-Fluoro-4-(4″-propylphenyl)-4′-propyltolan C-N point 85.7° C., N-I point 196.7° C.
2-Fluoro-4-(4″-butylphenyl)-4′-propyltolan C-N point 69.9° C., N-I point 182.7° C.
2-Fluoro-4-(4″-pentyphenyl)-4′-propyltolan C-N point 79.7° C., N-I point 184.76° C.
2-Fluoro-4-(4″-hexylphenyl)-4′-propyltolan
2-Fluoro-4-(4″-heptylphenyl)-4′-propyltolan
2-Fluoro-4-(4″-octylphenyl)-4′-propyltolan
2-Fluoro-4-(4″-nonylphenyl)-4′-propyltolan
2-Fluoro-4-(4″-decylphenyl)-4′-propyltolan
2-Fluoro-4-(4″-methylphenyl)-4′-butyltolan
2-Fluoro-4-(4″-ethylphenyl)-4′-butyltolan
2-Fluoro-4-(4″-propylphenyl)-4′-butyltolan
2-Fluoro-4-(4″-butylphenyl)-4′-butyltolan C-N point 63.7° C., N-I point 169.4° C.
2-Fluoro-4-(4″-pentylphenyl)-4′-butyltolan
2-Fluoro-4-(4″-hexylphenyl)-4′-butyltolan
2-Fluoro-4-(4″-heptylphenyl)-4′-butyltolan
2-Fluoro-4-(4″-octylphenyl)-4′-butyltolan
2-Fluoro-4-(4″-nonylphenyl)-4′-butyltolan
2-Fluoro-4-(4″-decylphenyl)-4′-butyltolan
2-Fluoro-4-(4″-methylphenyl)-4′-pentyltolan
2-Fluoro-4-(4″-ethylphenyl)-4′-pentyltolan
2-Fluoro-4-(4″-propylphenyl)-4′-pentyltolan C-N point 78.3° C., N-I point 184.9° C.
2-Fluoro-4-(4″-pentylphenyl)-4′-pentyltolan
2-Fluoro-4-(4″-hexylphenyl)-4′-pentyltolan
2-Fluoro-4-(4″-heptylphenyl)-4′-pentyltolan
2-Fluoro-4-(4″-octylphenyl)-4′-pentyltolan
2-Fluoro-4-(4″-nonylphenyl)-4′-pentyltolan
2-Fluoro-4-(4″-decylphenyl)-4′-pentyltolan
2-Fluoro-4-(4″-methylphenyl)-4′-hexyltolan
2-Fluoro-4-(4″-ethylphenyl)-4′-hexyltolan
2-Fluoro-4-(4″-propylphenyl)-4′-hexyltolan
2-Fluoro-4-(4″-butylphenyl)-4′-hexyltolan
2-Fluoro-4-(4″-pentylphenyl)-4′-hexyltolan
2-Fluoro-4-(4″-hexylphenyl)-4′-hexyltolan
2-Fluoro-4-(4″-heptylphenyl)-4′-hexyltolan
2-Fluoro-4-(4″-octylphenyl)-4′-hexyltolan
2-Fluoro-4-(4″-nonylphenyl)-4′-hexyltolan
2-Fluoro-4-(4″-decylphenyl)-4′-hexyltolan
2-Fluoro-4-(4″-methylphenyl)-4′-heptyltolan
2-Fluoro-4-(4″-ethylphenyl)-4′-heptyltolan
2-Fluoro-4-(4″-propylphenyl)-4′-heptyltolan
2-Fluoro-4-(4″-butylphenyl)-4′-heptyltolan
2-Fluoro-4-(4″-pentylphenyl)-4′-heptyltolan
2-Fluoro-4-(4″-hexylphenyl)-4′-heptyltolan
2-Fluoro-4-(4″-heptylphenyl)-4′-heptyltolan
2-Fluoro-4-(4″-octylphenyl)-4′-heptyltolan
2-Fluoro-4-(4″-nonylphenyl)-4′-heptyltolan
2-Fluoro-4-(4″-decylphenyl)-4′-heptyltolan
2-Fluoro-4-(4″-methylphenyl)-4′-octyltolan
2-Fluoro-4-(4″-ethylphenyl)-4′-octyltolan
2-Fluoro-4-(4″-propylphenyl)-4′-octyltolan
2-Fluoro-4-(4″-butylphenyl)-4′-octyltolan
2-Fluoro-4-(4″-pentylphenyl)-4′-octyltolan
2-Fluoro-4-(4″-hexylphenyl)-4′-octyltolan
2-Fluoro-4-(4″-heptylphenyl)-4′-octyltolan
2-Fluoro-4-(4″-octylphenyl)-4′-octyltolan
2-Fluoro-4-(4″-nonylphenyl)-4′-octyltolan
2-Fluoro-4-(4″-decylphenyl)-4′-octyltolan
2-Fluoro-4-(4″-methylphenyl)-4′-nonyltolan
2-Fluoro-4-(4″-ethylphenyl)-4′-nonyltolan
2-Fluoro-4-(4″-propylphenyl)-4′-nonyltolan
2-Fluoro-4-(4″-butylphenyl)-4′-nonyltolan
2-Fluoro-4-(4″-pentylphenyl)-4′-nonyltolan
2-Fluoro-4-(4″-hexylphenyl)-4′-nonyltolan
2-Fluoro-4-(4″-heptylphenyl)-4′-nonyltolan
2-Fluoro-4-(4″-octylphenyl)-4′-nonyltolan
2-Fluoro-4-(4″-nonylphenyl)-4′-nonyltolan
2-Fluoro-4-(4″-decylphenyl)-4′-nonyltolan
2-Fluoro-4-(4″-methylphenyl)-4′-decyltolan
2-Fluoro-4-(4″-ethylphenyl)-4′-decyltolan
2-Fluoro-4-(4″-propylphenyl)-4′-decyltolan
2-Fluoro-4-(4″-butylphenyl)-4′-decyltolan
2-Fluoro-4-(4″-pentylphenyl)-4′-decyltolan
2-Fluoro-4-(4″-hexylphenyl)-4′-decyltolan
2-Fluoro-4-(4″-heptylphenyl)-4′-decyltolan
2-Fluoro-4-(4″-octylphenyl)-4′-decyltolan
2-Fluoro-4-(4″-nonylphenyl)-4′-decyltolan
2-Fluoro-4-(4″-decylphenyl)-4′-decyltolan Example 5: Production of Compound (1-e):

Production of 4-(4″-pentylphenyl)-2′-fluoro-4′-cyanotolan:

Step (E-1):

87 g of 1-bromo-4′-pentylbiphenyl, 36 g of 3-methyl-1-butyn-3-ol, 1.2 g of triphenylphosphine and 0.62 g of bis (triphenylphosphine) palladium(II) chloride were dissolved in 300 ml of triethylamine in nitrogen atmosphere, and 0.2 g of copper(I) iodide was added thereto. This was stirred at room temperature for one hour and then at 90° C. for 5 hours. The reaction solution was poured into water, and the crystals as precipitated were filtered out and washed with water. The crystals thus obtained were dissolved in chloroform and washed two times with 10% hydrochloric acid and two times with water, and chloroform was removed by distillation. The residue was recrystallized from a mixed solvent of acetone and methanol to obtain 37 g of 3-methyl-1-(4″-pentylbiphenyl-4-yl)-1-butyn-3-ol.

Step (E-2):

37 g of 3-methyl-1-(4″-pentylbiphenyl-4-yl)-1-butyn-3-ol was dissolved in 250 ml of toluene in nitrogen atmosphere, and 1.5 g of sodium hydride (60% in paraffin liquid) was added thereto. This was stirred for 6 hours at 60° C. The reaction solution was poured into 1000 ml of water, extracted with chloroform and washed three times with water. Toluene and chloroform were removed by distillation, and the residue was recrystallized from methanol to obtain 30 g of 4-ethynyl-4′-pentylbiphenyl.

Step (E-3):

3.6 g of 4-bromo-2-fluoro-1-iodobenzene was dissolved in 4.4 ml of diethylamine in nitrogen atmosphere, and 0.04 g of bis (triphenylphosphine) palladium(II) chloride and 0.04 g of copper(I) iodide were added thereto and stirred. The flask containing the reaction mixture was cooled to 5° C. or lower, and a solution of 3 g of 4-ethynyl-4'-pentylbiphenyl as dissolved in 8 ml of diethylamine was dropwise added thereto. This was stirred at room temperature for 5 hours, and the reaction solution was poured into a mixture of 7 ml of concentrated hydrochloric acid and 100 g of ice. This was extracted with chloroform and washed two times with water, and chloroform was removed by distillation. The residue was recrystallized from a mixed solvent comprising acetone and chloroform to obtain 3.2 g of 4-(4''-pentylphenyl)-2'-fluoro-4'-bromotolan.

Step (E-4):

3.2 g of 4-(4''-pentylphenyl)-2'-fluoro-4'-bromotolan and 1 g of copper(I) cyanide were added to 16 ml of NMP and refluxed for 2 hours. The reaction solution was poured into a mixture of 4 g of iron(II) chloride, 1.2 ml of concentrated hydrochloric acid and 4.6 ml of water. The precipitated crystals were filtered out and washed with water. The thus obtained crystals were dissolved in chloroform and washed three times with water, and chloroform was removed by distillation. The residue was purified by silica gel-chloroform column chromatography and recrystallized from a mixed solvent comprising acetone and methanol to obtain 1.5 g of 4-(4''-pentylphenyl)-2'-fluoro-4'-cyanotolan. The compound had a crystal-smectic phase transition point (hereinafter referred to as C-Sm point) of 123.9° C., a smectic-nematic phase transition point (hereinafter referred to as Sm-N point) of 167.3° C. and an N-I point of 245.3° C.

In the same manner, the following compounds were produced:

4-(4''-Methylphenyl)-2'-fluoro-4'-cyanotolan
4-(4''-Ethylphenyl)-2'-fluoro-4'-cyanotolan C-Sm point 137.4° C., Sm-N point 175.1° C. N-I point 269.0° C.
4-(4''-Propylphenyl)-2'-fluoro-4'-cyanotolan C-Sm point 150.6° C., Sm-N point 185.1° C., N-I point 268.4° C.
4-(4''-Butylphenyl)-2-fluoro-4'-cyanotolan C-Sm point 120.9° C., Sm-N point 176.0° C., N-I point 250.1° C.
4-(4''-Hexylphenyl)-2'-fluoro-4'-cyanotolan
4-(4''-Heptylphenyl)-2'-fluoro-4'-cyanotolan
4-(4''-Octylphenyl)-2'-fluoro-4'-cyanotolan
4-(4''-Nonylphenyl)-2'-fluoro-4'cyanotolan
4-(4''-Decylphenyl)-2'-fluoro-4'cyanotolan Example 6: Production of Compound (1-f):

Production of 4-(4''-pentylphenyl)-2'-fluoro-4'-propyltolan:

Step (F-1):

1.5 g of 1-bromopropane was dissolved in 20 ml of THF in nitrogen atmosphere and dropwise added to 0.3 g of magnesium metal. After addition, this was stirred for 3 hours at room temperature to prepare a Grignard reagent. In another flask, 0.12 g of bis(1,3-diphenylphosphinopropane) nickel(II) chloride and 4.2 g of 4-(4''-pentylphenyl)-2'-fluoro-4'-bromotolan were dissolved in 16 ml of THF, and the previously prepared Grignard reagent was dropwise added thereto. This was stirred at room temperature overnight, and the reaction solution was poured into a mixture of 4 ml of concentrated hydrochloric acid and 32 g of ice. This was extracted with chloroform and washed three times each with water, and chloroform was removed by distillation. The residue was recrystallized from a mixed solvent comprising acetone and methanol, and the crystals thus obtained were purified by silica gel-chloroform column chromatography and again recrystallized from a mixed solvent of acetone and methanol to obtain 1.6 g of 4-(4''-pentylphenyl)-2'-fluoro-4'-propyltolan. The compound has a C-Sm point of 131.0° C., an Sm-N point of 72.5° C. and an N-I point of 198.3° C.

In the same manner, the following compounds were produced.

4-(4''-Methylphenyl)-2'-fluoro-4'-methyltolan
4-(4''-Ethylphenyl)-2'-fluoro-4'-methyltolan
4-(4''-Propylphenyl)-2'-fluoro-4'-methyltolan
4-(4''-Butylphenyl)-2'-fluoro-4'-methyltolan
4-(4''-Pentylphenyl)-2'-fluoro-4'-methyltolan
4-(4''-Hexylphenyl)-2'-fluoro-4'-methyltolan
4-(4''-Heptylphenyl)-2'-fluoro-4'-methyltolan
4-(4''-Octylphenyl)-2'-fluoro-4'-methyltolan
4-(4''-Nonylphenyl)-2'-fluoro-4'-methyltolan
4-(4''-Decylphenyl)-2'-fluoro-4'-methyltolan
4-(4''-Methylphenyl)-2'-fluoro-4'-ethyltolan
4-(4''-Ethylphenyl)-2'-fluoro-4'-ethyltolan
4-(4''-Propylphenyl)-2'-fluoro-4'-ethyltolan
4-(4''-Butylphenyl)-2'-fluoro-4'-ethyltolan
4-(4''-Pentylphenyl)-2'-fluoro-4'-ethyltolan
4-(4''-Hexylphenyl)-2'-fluoro-4'-ethyltolan
4-(4''-Heptylphenyl)-2'-fluoro-4'-ethyltolan
4-(4''-Octylphenyl)-2'-fluoro-4'-ethyltolan
4-(4''-Nonylphenyl)-2'-fluoro-4'-ethyltolan
4-(4''-Decylphenyl)-2'-fluoro-4'-ethyltolan
4-(4''-Methylphenyl)-2'-fluoro-4'-propyltolan
4-(4''-Ethylphenyl)-2'-fluoro-4'-propyltolan C-N point 163.6° C., N-I point 196.7° C.
4-(4''-Propylphenyl)-2'-fluoro-4'-propyltolan C-Sm point 131.0° C., Sm-N point 172.5° C. N-I point 198.3° C.
4-(4''-Butylphenyl)-2'-fluoro-4'-propyltolan
4-(4''-Hexylphenyl)-2'-fluoro-4'-propyltolan
4-(4''-Heptylphenyl)-2'-fluoro-4'-propyltolan
4-(4''-Octylphenyl)-2'-fluoro-4'-propyltolan
4-(4''-Nonylphenyl)-2'-fluoro-4'-propyltolan
4-(4''-Decylphenyl)-2'-fluoro-4'-propyltolan
4-(4''-Methylphenyl)-2'-fluoro-4'-butyltolan
4-(4''-Ethylphenyl)-2'-fluoro-4'-butyltolan
4-(4''-Propylphenyl)-2'-fluoro-4'-butyltolan
4-(4''-Butylphenyl)-2'-fluoro-4'-butyltolan
4-(4''-Pentylphenyl)-2'-fluoro-4'-butyltolan
4-(4''-Hexylphenyl)-2'-fluoro-4'-butyltolan
4-(4''-Heptylphenyl)-2'-fluoro-4'-butyltolan
4-(4''-Octylphenyl)-2'-fluoro-4'-butyltolan
4-(4''-Nonylphenyl)-2'-fluoro-4'-butyltolan
4-(4''-Decylphenyl)-2'-fluoro-4'-butyltolan
4-(4''-Methylphenyl)-2'-fluoro-4'-pentyltolan
4-(4''-Ethylphenyl)-2'-fluoro-4'-pentyltolan
4-(4''-Propylphenyl)-2'-fluoro-4'-pentyltolan
4-(4''-Butylphenyl)-2'-fluoro-4'-pentyltolan
4-(4''-Pentylphenyl)-2'-fluoro-4'-pentyltolan
4-(4''-Hexylphenyl)-2'-fluoro-4'-pentyltolan
4-(4''-Heptylphenyl)-2'-fluoro-4'-pentyltolan
4-(4''-Octylphenyl)-2'-fluoro-4'-pentyltolan
4-(4''-Nonylphenyl)-2'-fluoro-4'-pentyltolan
4-(4''-Decylphenyl)-2'-fluoro-4'-pentyltolan
4-(4''-Methylphenyl)-2'-fluoro-4'-hexyltolan
4-(4''-Ethylphenyl)-2'-fluoro-4'-hexyltolan
4-(4''-Propylphenyl)-2'-fluoro-4'-hexyltolan
4-(4''-Butylphenyl)-2'-fluoro-4'-hexyltolan
4-(4''-Pentylphenyl)-2'-fluoro-4'-hexyltolan
4-(4''-Hexylphenyl)-2'-fluoro-4'-hexyltolan
4-(4''-Heptylphenyl)-2'-fluoro-4'-hexyltolan
4-(4''-Octylphenyl)-2'-fluoro-4'-hexyltolan 4-(4″-Nonylphenyl)-2′-fluoro-4′-hexyltolan
4-(4″-Decylphenyl)-2′-fluoro-4′-hexyltolan
4-(4″-Methylphenyl)-2′-fluoro-4′-heptyltolan
4-(4″-Ethylphenyl)-2′-fluoro-4′-heptyltolan
4-(4″-Propylphenyl)-2′-fluoro-4′-heptyltolan
4-(4″-Butylphenyl)-2′-fluoro-4′-heptyltolan
4-(4″-Pentylphenyl)-2′-fluoro-4′-heptyltolan
4-(4″-Hexylphenyl)-2′-fluoro-4′-heptyltolan
4-(4″-Heptylphenyl)-2′-fluoro-4′-heptyltolan
4-(4″-Octylphenyl)-2′-fluoro-4′-heptyltolan
4-(4″-Nonylphenyl)-2′-fluoro-4′-heptyltolan
4-(4″-Decylphenyl)-2′-fluoro-4′-heptyltolan
4-(4″-Methylphenyl)-2′-fluoro-4′-octyltolan
4-(4″-Ethylphenyl)-2′-fluoro-4′-octyltolan
4-(4″-Propylphenyl)-2′-fluoro-4′-octyltolan
4-(4″-Butylphenyl)-2′-fluoro-4′-octyltolan
4-(4″-Pentylphenyl)-2′-fluoro-4′-octyltolan
4-(4″-Hexylphenyl)-2′-fluoro-4′-octyltolan
4-(4″-Heptylphenyl)-2′-fluoro-4′-octyltolan
4-(4″-Octylphenyl)-2′-fluoro-4′-octyltolan
4-(4″-Nonylphenyl)-2′-fluoro-4′-octyltolan
4-(4″-Decylphenyl)-2′-fluoro-4′-octyltolan
4-(4″-Methylphenyl)-2′-fluoro-4′-nonyltolan
4-(4″-Ethylphenyl)-2′-fluoro-4′-nonyltolan
4-(4″-Propylphenyl)-2′-fluoro-4′-nonyltolan
4-(4″-Butylphenyl)-2′-fluoro-4′-nonyltolan
4-(4″-Pentylphenyl)-2′-fluoro-4′-nonyltolan
4-(4″-Hexylphenyl)-2′-fluoro-4′-nonyltolan
4-(4″-Heptylphenyl)-2′-fluoro-4′-nonyltolan
4-(4″-Octylphenyl)-2′-fluoro-4′-nonyltolan
4-(4″-Nonylphenyl)-2′-fluoro-4′-nonyltolan
4-(4″-Decylphenyl)-2′-fluoro-4′-nonyltolan
4-(4″-Methylphenyl)-2′-fluoro-4′-decyltolan
4-(4″-Ethylphenyl)-2′-fluoro-4′-decyltolan
4-(4″-Propylphenyl)-2′-fluoro-4′-decyltolan
4-(4″-Butylphenyl)-2′-fluoro-4′-decyltolan
4-(4″-Pentylphenyl)-2′-fluoro-4′-decyltolan
4-(4″-Hexylphenyl)-2′-fluoro-4′-decyltolan
4-(4″-Heptylphenyl)-2′-fluoro-4′-decyltolan
4-(4″-Octylphenyl)-2′-fluoro-4′-decyltolan
4-(4″-Nonylphenyl)-2′-fluoro-4′-decyltolan
4-(4″-Decylphenyl)-2′-fluoro-4′-decyltolan Example 7: Liquid Crystal Composition Liquid crystal compositions (a) to (g) of the present invention were prepared, each containing ECH liquid crystals as base liquid crystals and compounds of the present invention as obtained in Examples 1 to 6 in the proportion mentioned below. For comparison, comparative liquid crystal compositions (h) to (j) were also prepared, each containing only known liquid crystal compounds in the proportion mentioned below.

TABLE 11

| Liquid Crystal Composition | a | b | c |
|---|---|---|---|
| 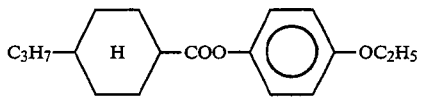 | 4.6 | 5.7 | 5.7 |
| 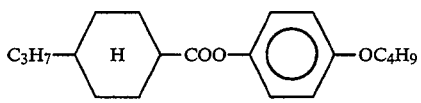 | 11.8 | 14.7 | 14.7 |
| 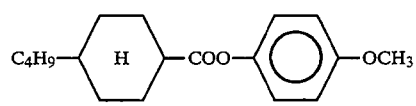 | 9.2 | 11.5 | 11.5 |
| 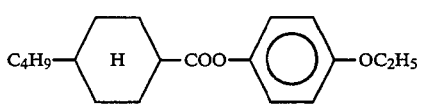 | 9.3 | 11.5 | 11.5 |
| 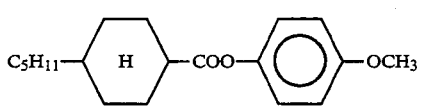 | 10.1 | 12.6 | 12.6 |
| 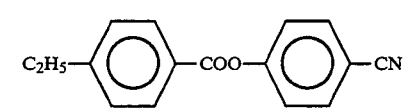 | 14.0 | 12.0 | 12.0 |
| 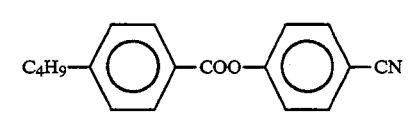 | 14.0 |  | 6.0 |
| 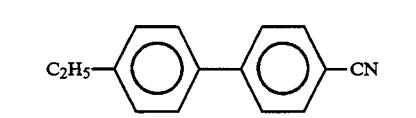 | 6.0 | 12.0 | 6.0 |

TABLE 11-continued
| Liquid Crystal Composition | a | b | c |
|---|---|---|---|
|  C$_4$H$_9$—⬡—⬡—CN | | | 6.0 |
| 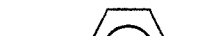 C$_4$H$_9$—⬡—C≡C—⬡(F)—⬡—C$_3$H$_7$ | | | 10.0 |
|  C$_3$H$_7$—⬡—C≡C—⬡(F)—⬡—C$_3$H$_7$ | | | 10.0 |
|  C$_5$H$_{11}$—⬡—C≡C—⬡(F)—⬡—C$_3$H$_7$ | | | 10.0 |
|  C$_3$H$_7$—⬡(F)—C≡C—⬡—⬡—C$_4$H$_9$ | | | 10.0 |
| 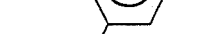 C$_3$H$_7$—⬡(F)—C≡C—⬡—⬡—C$_5$H$_{11}$ | | | 10.0 |
|  C$_4$H$_9$—⬡—⬡(F)—C≡C—⬡—CN | | | 5.0 |
(proportion: % by weight)
TABLE 12
| Liquid Crystal Composition | d | e | f | g |
|---|---|---|---|---|
| C$_3$H$_7$—⬢(H)—COO—⬡—OC$_2$H$_5$ | 6.4 | 5.4 | 4.6 | 5.9 |
| C$_3$H$_7$—⬢(H)—COO—⬡—OC$_4$H$_9$ | 16.5 | 13.9 | 12.1 | 15.3 |
| C$_4$H$_9$—⬢(H)—COO—⬡—OCH$_3$ | 12.9 | 10.9 | 9.4 | 11.9 |
| C$_4$H$_9$—⬢(H)—COO—⬡—OC$_2$H$_5$ | 13.0 | 10.9 | 9.5 | 11.9 |

TABLE 12-continued
| Liquid Crystal Composition | d | e | f | g |
|---|---|---|---|---|
| 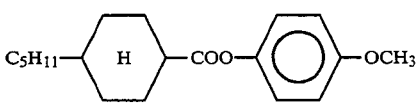 C5H11—H—COO—⟨⟩—OCH3 | 14.2 | 11.9 | 10.4 | 13.1 |
| 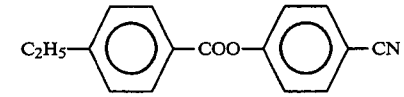 C2H5—⟨⟩—COO—⟨⟩—CN | 14.0 | 12.0 | 12.0 | 6.0 |
| 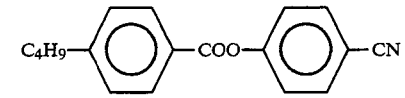 C4H9—⟨⟩—COO—⟨⟩—CN | | 6.0 | 12.0 | 6.0 |
| 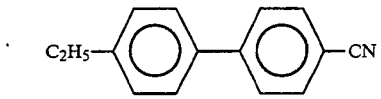 C2H5—⟨⟩—⟨⟩—CN | | 6.0 | | |
| 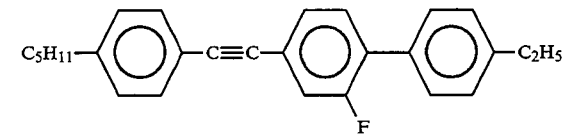 C5H11—⟨⟩—C≡C—⟨⟩(F)—⟨⟩—C2H5 | 9.0 | | | |
| 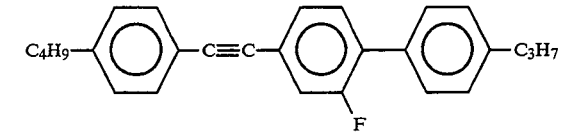 C4H9—⟨⟩—C≡C—⟨⟩(F)—⟨⟩—C3H7 | | | 10.0 | 10.0 |
| 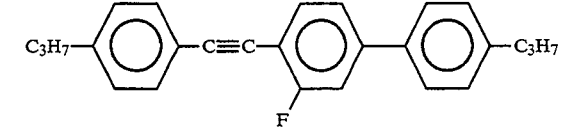 C3H7—⟨⟩—C≡C—⟨⟩(F)—⟨⟩—C3H7 | | | 10.0 | 10.0 |
| 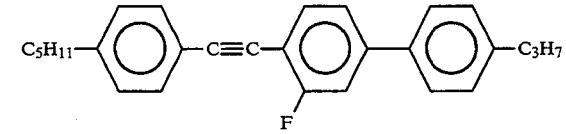 C5H11—⟨⟩—C≡C—⟨⟩(F)—⟨⟩—C3H7 | 9.0 | 9.0 | 10.0 | 10.0 |
| 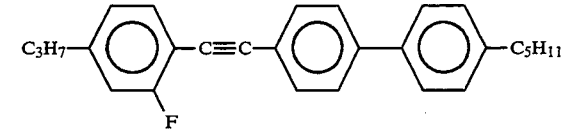 C3H7—⟨⟩(F)—C≡C—⟨⟩—⟨⟩—C5H11 | | 9.0 | | |
| 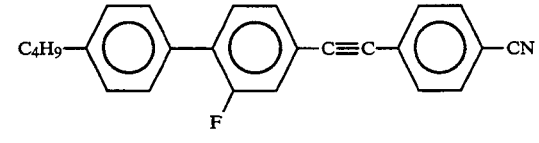 C4H9—⟨⟩—⟨⟩(F)—C≡C—⟨⟩—CN | | 5.0 | | |
| 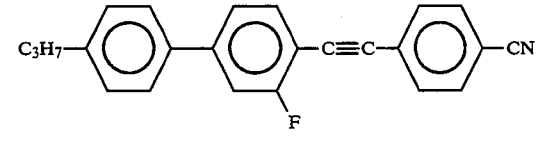 C3H7—⟨⟩—⟨⟩(F)—C≡C—⟨⟩—CN | | 5.0 | | |
(proportion: % by weight)

TABLE 13

| Liquid Crystal Composition | h | i | j |
|---|---|---|---|
| 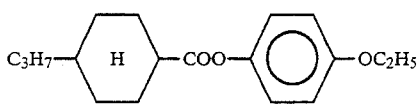 C₃H₇—H—COO—⬡—OC₂H₅ | 5.5 | 5.5 | 4.6 |
| 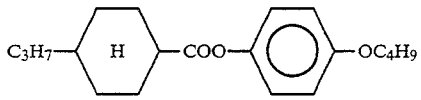 C₃H₇—H—COO—⬡—OC₄H₉ | 14.5 | 14.5 | 11.8 |
| 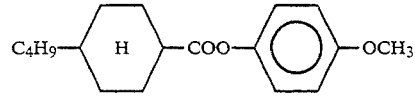 C₄H₉—H—COO—⬡—OCH₃ | 11.3 | 11.3 | 9.2 |
| 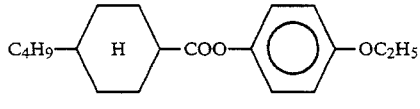 C₄H₉—H—COO—⬡—OC₂H₅ | 11.3 | 11.3 | 9.3 |
| 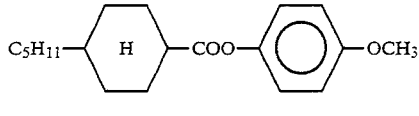 C₅H₁₁—H—COO—⬡—OCH₃ | 12.4 | 12.4 | 10.1 |
| 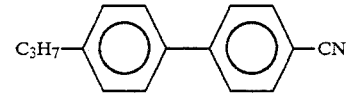 C₃H₇—⬡—⬡—CN | 5.0 | 5.0 | 5.0 |
| 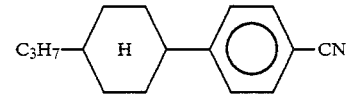 C₃H₇—H—⬡—CN | 5.0 | 10.0 | 10.0 |
| 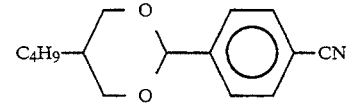 C₄H₉—(dioxane)—⬡—CN | 15.0 | 10.0 | 10.0 |
| 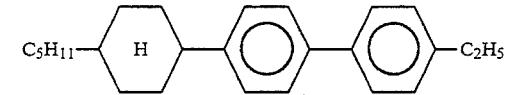 C₅H₁₁—H—⬡—⬡—C₂H₅ | 10.0 | | |
| 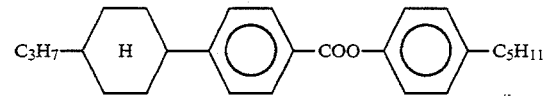 C₃H₇—H—⬡—COO—⬡—C₅H₁₁ | | 10.0 | 15.0 |
| 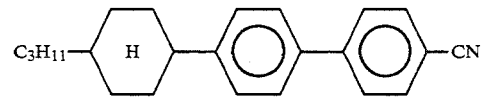 C₃H₁₁—H—⬡—⬡—CN | 10.0 | | 15.0 |
| 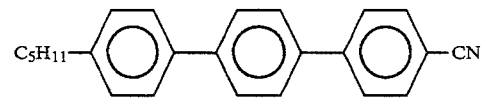 C₅H₁₁—⬡—⬡—⬡—CN | | 10.0 | |

(proportion: % by weight)

N-I point and Δn of each of compositions (a) to (j) were measured and the data obtained are presented in Table 14:

TABLE 14

| Liquid Crystal Composition | a | b | c | d | e |
|---|---|---|---|---|---|
| N-I Point (°C.) | 63.4 | 76.6 | 75.2 | 82.4 | 80.9 |

TABLE 14-continued

| Δn | 0.158 | 0.168 | 0.164 | 0.159 | 0.175 |
|---|---|---|---|---|---|
| Liquid Crystal Composition | f | g | h | i | j |
| N-I Point (°C.) | 86.5 | 91.7 | 79.2 | 80.1 | 92.6 |
| Δn | 0.189 | 0.182 | 0.119 | 0.127 | 0.128 |

From the above data, it is understood that liquid crystal compositions (a) to (g) containing compounds of the present invention have a higher Δn value by 0.04 to 0.06 than liquid crystal compositions (h) to (j) comprising only known liquid crystal compounds.

Example 8: Liquid Crystal Display Device

FIG. 1 depicts a liquid crystal display device. An electrode 3 of a transparent conductive coating (e.g., ITO coating) was formed on each of glass substrates 1 and 2, and an aligning coating of polyimide or the like was coated over the electrode. Next, this was rubbed to form an aligning coating layer 4. The glass substrates 1 and 2 were then positioned to face each other via a sealant 6, and one of liquid crystal compositions (a) to (j) as prepared in Example 7 was injected into the space between the glass substrates. A polarizing plate was attached to the outer surface of the substrate 1 and a reflective polarizing plate to the outer surface of the substrate 2. Thus, TN type liquid crystal display cells A to J were formed. The cell gap d in each liquid crystal display cell was determined in such a way that the value of Δn•d of each cell falls within the range of from 1.2 to 1.3.

The thus formed liquid crystal display cells were driven by an alternating current static driving system, and the threshold voltage at 25° C. (hereinafter referred to as $V_{th}$), the visible angle dependence of voltage-transmittance (hereinafter referred to as $\alpha$), the sharpness (hereinafter referred to as $\beta$), the rise time (hereinafter referred to as Tr) and the decay time (hereinafter referred to as Td) were measured by reflection measurement. $\alpha$, $\beta$ and $V_{th}$ are defined by the following expressions:

$$\alpha = \frac{V_{10}\,(\theta = 80°,\ T = 25°\,C.)}{V_{10}\,(\theta = 50°,\ T = 25°\,C.)}$$

$$\beta = \frac{V_{10}\,(\theta = 80°,\ T = 25°\,C.)}{V_{90}\,(\theta = 80°,\ T = 25°\,C.}$$

where: $V_{th} = V_{10}$;

$\theta$: angle of incident rays to cell (the vertical direction to panel is 90°); and $V_{10}$, $V_{90}$: voltage at transmittance of 10% and 90%, respectively.

Tr represents the time necessary to lower the transmittance to 10% when the voltage was on (the voltage applied was $V_{90}$ ($\theta = 80°$)), and Td represents the time necessary to recover the transmittance of 90% when the voltage was off (the voltage applied was $V_{10}$ ($\theta = 80°$)). The results of the measurement are presented in Table 15.

TABLE 15

| Liquid Crystal Panel | A | B | C | D | E |
|---|---|---|---|---|---|
| Liquid Crystal Composition | a | b | c | d | e |

TABLE 15-continued

| Cell Thickness (μ) | 8.0 | 8.0 | 8.0 | 8.0 | 7.0 |
|---|---|---|---|---|---|
| Δnd | 1.26 | 1.34 | 1.31 | 1.27 | 1.23 |
| $V_{th}$ (V) | 1.214 | 1.747 | 1.664 | 2.005 | 1.530 |
| α | 1.193 | 1.158 | 1.170 | 1.161 | 1.190 |
| β | 1.270 | 1.256 | 1.255 | 1.248 | 1.254 |
| Tr (ms) | 114 | 95 | 95 | 100 | 77 |
| Td (ms) | 150 | 131 | 125 | 139 | 110 |
| Tr + Td (ms) | 264 | 226 | 220 | 239 | 187 |
| Liquid Crystal Panel | F | G | H | I | J |
| Liquid Crystal Panel | f | g | h | i | j |
| Cell Thickness (μ) | 7.0 | 7.0 | 10.0 | 10.0 | 10.0 |
| Δnd | 1.32 | 1.27 | 1.19 | 1.27 | 1.28 |
| $V_{th}$ (V) | 1.635 | 2.396 | 1.645 | 667 | 1.719 |
| α | 1.170 | 1.140 | 1.170 | 1.169 | 1.186 |
| β | 1.252 | 1.238 | 1.259 | 1.256 | 1.269 |
| Tr (ms) | 85 | 88 | 128 | 139 | 141 |
| Td (ms) | 108 | 109 | 189 | 191 | 196 |
| Tr + Td (ms) | 193 | 197 | 317 | 330 | 337 |

From the results presented in Table 15, it is understood that the liquid crystal cells A to G each having the liquid crystal composition containing liquid crystal compounds of the present invention have a higher (Tr + Td) value by 50 to 150 ms or so than the comparative liquid crystal cells H to J each comprising only known liquid crystal compounds.

In the present example, a TN type liquid crystal display cell was used, but the same results were obtained when an STN type display cell was used.

While the present invention has been disclosed in connection with preferred embodiments thereof, it should be appreciated that there are other embodiments of the present invention which fall within the spirit and scope of the present invention as defined by the appended claims.

What is claimed is:

1. A tolan derivative of a formula:

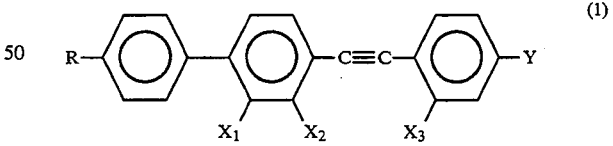

(1)

where R represents a linear alkyl group having from 1 to 10 carbon atoms; $X_1$, $X_2$ and $X_3$ independently represent a fluorine atom or a hydrogen atom, provided that one of them is necessarily a fluorine atom and the others are hydrogen atoms; and Y represents a nitrile group.

2. The tolan derivative according to claim 1, wherein $X_1$ is F and Y is a nitrile group.

3. The tolan derivative according to claim 1, wherein $X_2$ is F and Y is a nitrile group.

4. The tolan derivative according to claim 1, wherein $X_3$ is F and Y is a nitrile group.

5. A liquid crystal composition containing at least one tolan derivative of a formula:

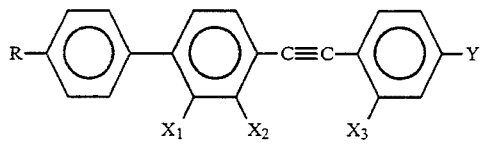
(1)

where R represents a linear alkyl group having from 1 to 10 carbon atoms; $X_1$, $X_2$ and $X_3$ independently represent a fluorine atom or a hydrogen atom, provided that one of them is necessarily a fluorine atom and the others are hydrogen atoms; and Y represents a nitrile group.

6. The liquid crystal composition according to claim 5, wherein said composition comprises from 5 to 50% by weight of at least one said tolan derivative; and further comprises from 30 to 80% by weight of at least one phenyl cyclohexanecarboxylate derivative of a formula:

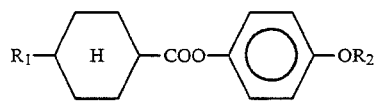

where $R_1$ and $R_2$ independently represent linear alkyl groups having from 1 to 10 carbon atoms; and the cyclohexane ring in the formula is in the trans-configuration.

7. The liquid crystal composition according to claim 5, wherein said composition comprises from 10 to 35% by weight of at least one said tolan derivative; and further comprises from 40 to 70% by weight of at least one phenyl cyclohexanecarboxylate derivative of a formula:

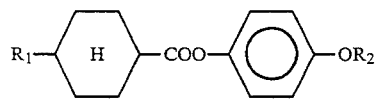

where $R_1$ and $R_2$ independently represent linear alkyl groups having from 1 to 10 carbon atoms; and the cyclohexane ring in the formula is in the trans-configuration; and from 10 to 50% by weight of at least one compound having positive dielectric anisotropy of a formula:

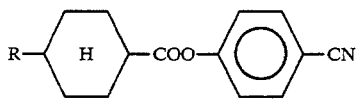

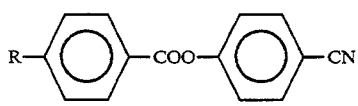

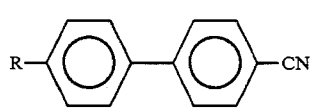

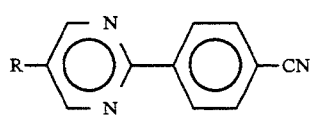

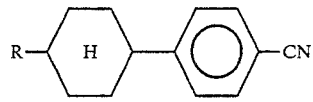

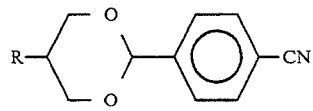

where R represents a linear alkyl group having from 1 to 10 carbon atoms; and the cyclohexane ring in the formula is in the trans-configuration.

8. A liquid crystal display device having a liquid crystal composition containing at least one tolan derivative of a formula:

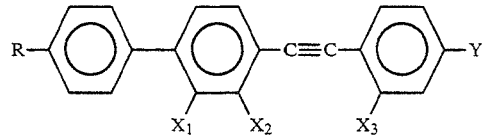
(1)

where R represents a linear alkyl group having from 1 to 10 carbon atoms; $X_1$, $X_2$ and $X_3$ independently represent a fluorine atom or a hydrogen atom, provided that one of them is necessarily a fluorine atom and the others are hydrogen atoms; and Y represents a nitrile group.

9. A liquid crystal display device according to claim 8, wherein said composition comprises from 5 to 50% by weight of at least one said tolan derivative; and further comprises from 30 to 80% by weight of at least one phenyl cyclohexanecarboxylate derivative of a formula:

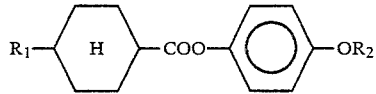

where $R_1$ and $R_2$ independently represent linear alkyl groups having from 1 to 10 carbon atoms; and the cyclohexane ring in the formula is in the trans-configuration.

10. A liquid crystal display device according to claim 8, wherein said composition comprises from 10 to 35% by weight of at least one said tolan derivative; and further comprises from 40 to 70% by weight of at least one phenyl cyclohexanecarboxylate derivative of a formula:

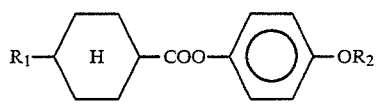

where $R_1$ and $R_2$ independently represent linear alkyl groups having from 1 to 10 carbon atoms; and the cyclohexane ring in the formula is in the trans-configuration; and from 10 to 50% by weight of at least one compound having positive dielectric anisotropy of a formula:

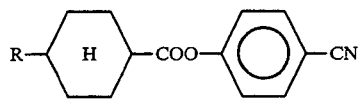
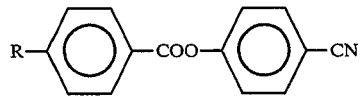
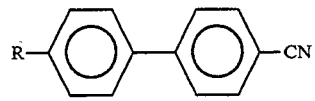
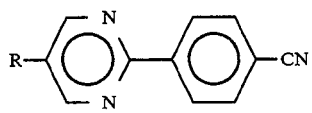
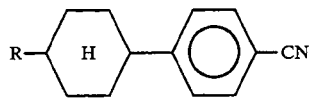
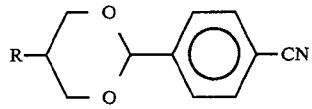
where R represents a linear alkyl group having from 1 to 10 carbon atoms; and the cyclohexane ring in the formula is in the trans-configuration.
* * * * *